(12) United States Patent
Creasy et al.

(10) Patent No.: US 11,318,050 B2
(45) Date of Patent: May 3, 2022

(54) NAVIGATION ASSISTANCE FOR THE VISUALLY IMPAIRED

(71) Applicant: American Printing House for the Blind, Inc., Louisville, KY (US)

(72) Inventors: Daniel Keith Creasy, Louisville, KY (US); John Karr, New Albany, IN (US); Mark Klarer, Louisville, KY (US); Rob Meredith, Louisville, KY (US); Larry Skutchan, Louisville, KY (US); Joe Wegner, Bedford, KY (US)

(73) Assignee: American Printing House for the Blind, Inc., Louisville, KY (US)

( * ) Notice: Subject to any disclaimer, the term of this patent is extended or adjusted under 35 U.S.C. 154(b) by 341 days.

(21) Appl. No.: 16/254,780

(22) Filed: Jan. 23, 2019

(65) Prior Publication Data

US 2019/0224049 A1 Jul. 25, 2019

Related U.S. Application Data

(60) Provisional application No. 62/709,635, filed on Jan. 24, 2018.

(51) Int. Cl.
*G01C 21/00* (2006.01)
*A61F 9/08* (2006.01)
(Continued)

(52) U.S. Cl.
CPC ............... *A61F 9/08* (2013.01); *A61H 3/061* (2013.01); *A61H 3/066* (2013.01);
(Continued)

(58) Field of Classification Search
CPC .......... A61H 3/06; A61H 3/061; A61H 3/063; A61H 3/068; A61H 2201/5092;
(Continued)

(56) References Cited

U.S. PATENT DOCUMENTS

| 5,642,303 A | 6/1997 | Small et al. |
| 5,806,017 A | 9/1998 | Hancock |

(Continued)

FOREIGN PATENT DOCUMENTS

| CN | 102741892 A | 10/2012 |
| CN | 106491320 A | 3/2017 |

(Continued)

OTHER PUBLICATIONS

A computer vision system that ensure the autonomous navigation of blind people; Ruxandra Tapu;Bogdan Mocanu;Titus Zaharia; 2013 E-Health and Bioengineering Conference (EHB); IEEE Conference Paper. (Year: 2013).*

(Continued)

*Primary Examiner* — Cuong H Nguyen
(74) *Attorney, Agent, or Firm* — Frost Brown Todd LLC

(57) ABSTRACT

A software application and system may be configured to enable a smartphone or other device to be used by a visually impaired person to receive voice navigation guidance during a directed exploration of an area. Directed exploration uses combinations of location data, directional data, and orientation data from the configured device to determine a direction that user wishes to explore, and only providing narrated results for streets, businesses, and other points of interest in that direction. The system may also utilize sets of wireless indicators positioned within indoor areas to provide accurate positioning to particular locations and floors within buildings.

19 Claims, 8 Drawing Sheets

(51) Int. Cl.
*G06F 3/16* (2006.01)
*A61H 3/06* (2006.01)
*G01C 21/36* (2006.01)
*G01C 21/20* (2006.01)
*G06F 3/0484* (2022.01)

(52) U.S. Cl.
CPC ..... *G01C 21/3629* (2013.01); *G01C 21/3644* (2013.01); *G01C 21/3652* (2013.01); *G06F 3/16* (2013.01); *A61H 2003/065* (2013.01); *A61H 2201/5046* (2013.01); *A61H 2201/5048* (2013.01); *A61H 2201/5064* (2013.01); *A61H 2201/5097* (2013.01); *G01C 21/206* (2013.01); *G06F 3/0484* (2013.01)

(58) Field of Classification Search
CPC .... A61H 2201/5064; A61H 2201/5043; G09B 21/001; G01L 21/16; G01C 21/20; G01C 21/206
USPC ....... 340/539.12, 539.13, 944; 701/412, 416, 701/419
See application file for complete search history.

(56) References Cited

U.S. PATENT DOCUMENTS

| | | | |
|---|---|---|---|
| 6,320,496 B1 | 11/2001 | Sokoler et al. | |
| 6,418,372 B1* | 7/2002 | Hofmann | G01C 21/20 701/434 |
| 7,039,522 B2 | 5/2006 | Landau | |
| 7,620,493 B2* | 11/2009 | Stankiewicz | G01C 21/206 340/539.13 |
| 8,504,288 B2* | 8/2013 | Kadous | G09B 29/106 701/433 |
| 8,548,738 B1* | 10/2013 | Kadous | G01C 21/206 701/434 |
| 8,731,817 B2 | 5/2014 | Ballew et al. | |
| 8,812,015 B2* | 8/2014 | Das | G01C 21/20 455/456.1 |
| 8,818,706 B1* | 8/2014 | Ogale | G01C 21/206 701/409 |
| 8,878,666 B2 | 11/2014 | Chu | |
| 8,937,554 B2 | 1/2015 | Kwan et al. | |
| 8,938,257 B2* | 1/2015 | Chao | G01S 5/16 455/456.1 |
| 9,014,721 B2* | 4/2015 | Das | H04W 4/029 455/456.2 |
| 9,204,251 B1 | 12/2015 | Mendelson | |
| 9,326,103 B2* | 4/2016 | Shen | G01C 21/005 |
| 9,726,746 B2 | 8/2017 | Said | |
| 9,810,538 B2* | 11/2017 | Marimuthu | G01C 21/206 |
| 9,906,909 B2 | 2/2018 | Sahadi et al. | |
| 10,248,379 B2* | 4/2019 | Steinberg | G06Q 10/10 |
| 10,656,905 B2* | 5/2020 | Steinberg | G06Q 10/10 |
| 2006/0125693 A1 | 6/2006 | Recker | |
| 2006/0247849 A1* | 11/2006 | Mohsini | G01C 21/20 701/434 |
| 2006/0293839 A1* | 12/2006 | Stankieiwcz | G01C 21/20 701/434 |
| 2011/0307172 A1* | 12/2011 | Jadhav | G01S 19/14 701/491 |
| 2013/0045751 A1* | 2/2013 | Chao | G01S 5/16 455/456.1 |
| 2015/0018018 A1* | 1/2015 | Shen | G01C 21/005 455/457 |
| 2015/0330787 A1 | 11/2015 | Cioffi et al. | |
| 2016/0124707 A1* | 5/2016 | Ermilov | G06F 9/451 345/156 |
| 2017/0010099 A1 | 1/2017 | Simcik | |
| 2017/0038792 A1* | 2/2017 | Moore | G06F 1/1683 |
| 2017/0162076 A1 | 6/2017 | Kanuganti et al. | |
| 2017/0312916 A1* | 11/2017 | Williams | G05D 1/0251 |
| 2017/0339642 A1 | 11/2017 | Bakker | |
| 2018/0202813 A1 | 7/2018 | Belt et al. | |
| 2018/0255426 A1 | 9/2018 | Liao et al. | |
| 2019/0034157 A1* | 1/2019 | Steinberg | G06Q 10/10 |
| 2019/0179601 A1* | 6/2019 | Steinberg | G06Q 50/30 |
| 2019/0212151 A1* | 7/2019 | Parker | G06F 3/048 |
| 2020/0261302 A1* | 8/2020 | Mitra | A61H 3/066 |

FOREIGN PATENT DOCUMENTS

| | | |
|---|---|---|
| JP | 2002-109680 | 4/2002 |
| KR | 2011-0003102 | 3/2011 |
| RU | 2503436 | 1/2014 |

OTHER PUBLICATIONS

Automatic generation of indoor navigation instructions for blind users using a user-centric graph; Hao Dong;Aura Ganz; 2014 36th Annual International Conference of the IEEE Engineering in Medicine and Biology Society; IEEE Conference Paper. (Year: 2014).*
Pedestrian dead reckoning: A basis for personal positioning; S Beauregard, H Haas—Proceedings of the 3rd Workshop on . . . , 2006—ave.dee.isep.ipp.pt. (Year: 2006).*
Bohonos, S., et al., Universal Real-Time Navigation Assistance (URNA): An urban Bluetooth beacon for the blind, Proc. of the 1st ACM SIGMOBILE Int, Workshop on Systems and Networking Support for Healthcare and Assisted Leaving Environments, pp. 83-88, 2007. (Year: 2007).*
Bourbakis, N., Sensing Surrounding 3D Space for Navigation of the Blind, IEEE Engineering in Medicine and Biology Magazine, pp. 49-55, 2008. (Year: 2008).*
Blind MuseumTourer: A System for Self-Guided Tours in Museums and Blind Indoor Navigation; by Apostolos Meliones et al., from https://www.mdpi.com/2227-7080/6/1/4 (Technologies 2018, 6(1), 4; https://doi.org/10.3390/technologies6010004).*
Multitarget Three Dimensional Indoor Navigation on a PDA in a Wireless Sensor Network.*
"A computer vision system that ensure the autonomous navigation of blind people" by Ruxandra Tapu;Bogdan Mocanu;Titus Zaharia; 2013 E-Health and Bioengineering Conference (EHB); Publisher: IEEE (Year: 2013).*
"A Novel Indoor Navigation System for Visually Impaired People" by Parth Mehta et al., International Conference on Computer Systems and Technologies—CompSysTech'11 Jun. 16-17, 2011, Vienna, Austria.*
An abstract for "Automatic generation of indoor navigation instructions for blind users using a user-centric graph" by Hao Dong, Aura Ganz; Annu Int Conf IEEE Eng Med Biol Soc. 2014 (2014:902-5. ).*
https://www.afb.org/afbpress/pubnew.asp?DocID=aw170905, accessed Jun. 17, 2021.
http://www.mdpi.com/2227-7080/6/1/4/pdf, accessed Jun. 17, 2021.
http://scholarworks.csun.edu/bitstream/handle/10211.3/202986/JTPD-2018-ID07-p62-82.pdf?sequence=1, accessed Jun. 17, 2021.
https://www.politesi.polimi.it/bitstream/10589/135024/1/2017_07_Rota_Montalto.pdf, accessed Jun. 17, 2021.
http://pages.silabs.com/rs/634-SLU-379/images/Whitepaper-Developing-Beacons-with-Bluetooth-Low-Energy-Technology.pdf, accessed Jun. 17, 2021.
http://www.clickandgomaps.com/clickandgo-nextgen-talking-signs, accessed Jun. 17, 2021.
https://searchcio.techtarget.com/feature/Indoor-navigation-system-transforms-working-conditions-for-the-blind, accessed Jun. 17, 2021.
Chenaghi, et al. "Guide Beacon: Beacon-based indoor wayfinding for the blind, visually impaired, and disoriented." (2017).
Chumkamon, et al. "A blind navigation system using RFID for indoor environments." (Jun. 2008).

* cited by examiner

NAVIGATION ASSISTANCE FOR THE VISUALLY IMPAIRED

PRIORITY

This application claims the benefit of U.S. provisional patent application 62/709,635, filed Jan. 24, 2018, the entirety of which is hereby incorporated by reference.

FIELD

The disclosed technology pertains to a system for providing navigational information to the visually impaired.

BACKGROUND

Among the challenges faced by the visually impaired is the difficulty of traveling and navigating to an intended destination, which can be difficult even in familiar settings. Within a building or neighborhood that a visually impaired person routinely navigates, a white cane or other tactile sensory tool may be adequate for testing a familiar path for unexpected obstacles. However, when traveling to new and unfamiliar areas a visually impaired person may desire more sophisticated navigational aids in order to have a sense of freedom of movement without the fear of becoming lost. While a white cane will help them to avoid obstacles in their path and sense the quality of the terrain, it will not help them reorient themselves if they have an incomplete or inaccurate spatial sense of the surrounding roads, buildings, and other landmarks.

Conventional tools that utilize software and technology to provide navigational aid, such as a handheld GPS for walking or hiking that provides voice prompts directed to a particular destination, are generally directed towards a more general audience of users, rather than being specifically tailored for the visually impaired. As such, the interfaces, features, and other capabilities are often not ideal for use by the visually impaired. For example, some voice guided navigation may use a combination of an on-screen map and voice prompts, such that a voice command to "turn right at next corner" may have little value when not paired with a visual map showing the pedestrian's position relative to the next corner.

Even where voice guidance is complete and separable from other features that require visual examination, it is still limited in the sense that it provides a directed navigational experience, rather than an exploratory one. For example, a fully descriptive, voice only navigation experience that provides frequent prompts for distance to next waypoint and instructions at each waypoint still provides a limited amount of freedom for the visually impaired since they are being navigated from their present location to a destination, with little context on what exists between or around those locations. While being able to navigate to a certain predetermined destination provides some freedom of movement, the ability to explore a city or even an indoor area such as a museum or retail location and perceive nearby points of interest that have not been previously selected or predetermined as destinations is still missing.

Another limitation of many conventional navigation aids is a reliance upon location providing devices and features that are always enabled, such as a global positioning system or GPS receiver, even where the user is in an area where the GPS signals cannot be received. This can lead to unnecessary power consumption from a battery of the navigational aid, and can limit a visually impaired person's ability to take extended trips with a navigational aid.

What is needed, therefore, is an improved system for providing navigational information to the visually impaired.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The inventors have conceived of novel technology that, for the purpose of illustration, is disclosed herein as applied in the context of navigation aids for the visually impaired. While the disclosed applications of the inventors' technology satisfy a long-felt but unmet need in the art of navigation aids for the visually impaired, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

Existing software systems do not provide the unconventional capabilities, features, and tools disclosed herein in any arrangement, and especially not in the unconventional combinations and arrangements disclosed herein. One or more of the disclosed features, tools, interfaces, or combinations and arrangements thereof may be implemented to advantageously provide an improved interface and feature set for providing navigational assistance to the visually impaired, while also reducing unnecessary power consumption by a configured navigation device. By providing combinations of interfaces and features according to one or more of the methods disclosed herein, the functioning of a computer, mobile computing device, or other device including a processor providing the interface is improved such that a subset of needed information can be determined from large datasets and provided to a visually impaired person in near real-time.

Figure 1:
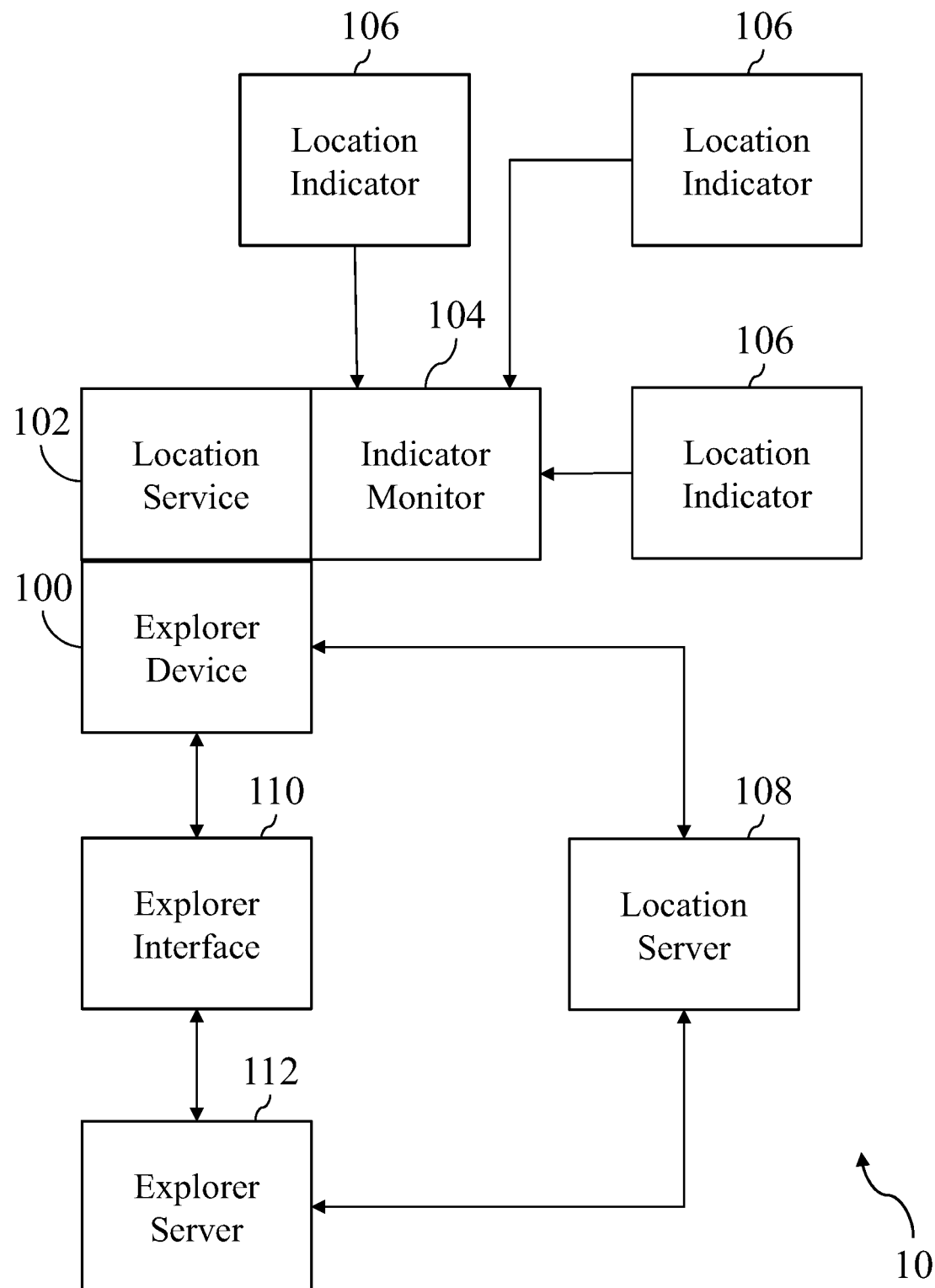
FIG. 1 shows a schematic diagram of an exemplary explorer system for providing navigation assistance to the visually impaired.

Turning now to the figures, FIG. 1 shows an exemplary explorer system (10) for providing navigation assistance to the visually impaired. Unlike conventional navigation aids, the explorer system (10) may be used by a visually impaired person to explore and navigate areas, with or without a particular destination having been pre-configured. As a result, rather than being limited to navigation directly to a destination that was selected prior to leaving from an origin point, the visually impaired person can explore their surroundings, with or without a destination point, and receive navigational cues about surrounding streets, locations, and other points of interest much in the way that a sighted person can.

The exemplary implementation of the explorer system (10) shown in FIG. 1 includes an explorer device (100), which may be, for example, a smartphone, tablet, a proprietary device, or another mobile computing device having such features as a user interface (e.g., a touch screen display, a keypad, voice inputs), a processor and memory for storing and executing software instructions to control various features of the device, communication devices (e.g., for communicating with wireless networks of various types), a battery or other power source, audio devices (e.g., a speaker, microphone, headphone), and other similar features such as those found in smartphones, tablets, and other mobile and wearable devices.

In particular, the explorer device (100) includes a location service (102) that is configured to provide the device with information on its current location and orientation, and an indicator monitor (104) that is configured to search for, detect, and connect to one or more location indicators (106) when they are within a detectable range. The location service (102) may include one or more devices and software features such as a global positioning device, an accelerometer, a gyroscope, a compass, and other features. In varying implementations, such features may be implemented using hardware (e.g., such as a global positioning system receiver that receives signals and determines a latitude and longitude based thereon), software (e.g., such as a software program that receives local wireless signals or transmissions that are unique to that area and determines a latitude and longitude based thereon), or both.

The indicator monitor (104) may be, for example, a Bluetooth transceiver, Wi-Fi transceiver, RFID transceiver, or other short or near-range wireless transceiver that can detect and communicate with a nearby location indicator (106). The location indicator (106) may include a memory and a communication device, and may be, for example, a device providing a Wi-Fi network or allowing direct Wi-Fi communication, a Bluetooth device, a wireless Bluetooth beacon, a Bluetooth LE beacon, an infrared emitter, or other similar device. As one example, the location indicator (106) could be implemented using the "iBeacon" protocol and devices. As will be apparent, the specifics of a particular implementation of the indicator monitor (104) and the location indicator (106) will be dependent upon each other in order to allow communication. The location indicators (106) may be placed in various locations to aid the explorer device (100) in navigating within spaces where GPS based navigation or other location services are unavailable or unreliable (e.g., such as within a structure that blocks outside wireless signals, or within a multi-level structure where the GPS information indicates a location but not an elevation), and may also be placed in order to provide more accurate and more proximate navigational cues (e.g., such as where a location indicator (106) may be placed directly on a water fountain or other amenity in order to provide a more accurate relative position than GPS or another aspect of the location service (102)).

The explorer system (10) also includes an explorer interface (110), an explorer server (112), and a location server (108). The explorer interface (110) may be, for example, a software application that is received from the explorer server (112) directly (e.g., such as downloading from a web site or file transfer location) or indirectly (e.g., such as downloading from a software or application store or third-party service) and installed on the explorer device (100). As another example, the explorer interface (110) may be a web service, web application, or web site provided by the explorer server (112) and accessed using a browser or other software application of the explorer device (100).

The location server (108) is configured to store and provide information relating to geographic locations (e.g., maps and geographic information for cities, states, countries, etc.), structures (e.g., locations and names of structures, floorplans, access door, parking areas) within geographic locations, and other points of interest ("POI") within geographic locations and structures (e.g., type, description, availability, location, identification of an associated location indicator (106)). When used herein, a POI should be understood to broadly refer to any physical or abstract object, such as a structure, item, attribute, or characteristic that may be located within or associated with a location. Thus, a reference within the descriptions or claims to a POI or, in the context of a POI, an "object" or "mapped object", could include, for example, a structure such as a restaurant, an item such as a statue or water fountain, a feature of a location such as a designation as an intersection, or an attribute or characteristic associated with a location such as an enforced speed limit or a designation as a public park. This information from the location server (108) may be used by the explorer device (100), and in conjunction with information from the location service (102) and the indicator monitor (104) in order to gather information about the surrounding geographic area, structures, and other mapped objects in and around those areas. One example of a location server (108) is "OpenStreetMap" or "OSM", which is a software project and data repository that organizes information on streets, sidewalks, crosswalks, structures, businesses, geographic features, and other mapped objects. The location server (108) may be queried (e.g., using latitude and longitude, identifying text, identification numbers, or other information) to gather information on objects such as their location and description.

As an example, the location service (102) may be used to provide location information (e.g., latitude and longitude), which may be used with information from the location server (108) to determine streets, structures, and other mapped objects that are within a certain radius of the location information. As another example, the indicator monitor (104) may automatically connect with a location indicator (106) that has been placed near a mapped object and receive a unique identifier from the location indicator (106). This unique identifier may be used with information from the location server (108) to determine a description, type, availability, and other features associated with that nearby mapped object, or to determine other mapped objects that are proximate to or otherwise associated with that mapped object. In some implementations, the indicator monitor (104) may also be operable to determine a distance between the indicator monitor (104) and the location indicator (106), which may be determined based upon a measured signal strength of a wireless signal received from the location indicator (106) and a calibrated or known rate at which such wireless signals lose strength after transmission.

In some implementations of the explorer interface (110), the explorer device (100) may be used for navigation without ongoing communication with the explorer server (112) or location server (108), in effect allowing it to be used in an offline mode. In such implementations, the explorer interface (110) may be packaged with any necessary information from the explorer server (112) and the location server (108), or may update those datasets from time to time when a reliable internet connection is available, in order to provide a seamless navigation experience in the future regardless of the availability of a network connection.

It should be understood that the explorer system (10) is an example only, and varying implementations of the technology disclosed herein may have different and/or additional components. For example, in some implementations the location server (108) and explorer server (112) may be the same server or server environment, or there may be no explorer server (112) and all necessary information will be packaged with an application downloaded from a third party software or app store.

The features and configuration of the explorer device (100) and explorer interface (110), as well as the functionality of the location indicators (106) and the location server (108) enable a visually impaired person to directionally "explore" areas around them, and seamlessly transition from a software mode and dataset appropriate for outdoor exploration to a software mode and dataset appropriate for indoor exploration. Directional exploration of surroundings may use the location service (102) to determine, for example, the location and direction that an explorer device (100) is facing (e.g., location may be determined using GPS capabilities, while direction may be determined using a software or hardware compass). In this manner, the explorer interface (110) can produce audio narration describing only those streets, structures, or other mapped objects that the visually impaired person is directing the explorer device (100) at, rather than announcing the presence of every object within a certain radius. This may be advantageous in that it allows the visually impaired person to develop a spatial sense of their surroundings in a way that can be related to particular directions, rather than being overwhelmed by information on every surrounding object with no indication of each object's direction. However, the explorer interface (110) can also support omnidirectional exploration in addition to directional exploration through various control or interface types.

For example, the explorer interface (110) may support several distinct types of exploration, which may be selected by a visually impaired person without requiring direct interaction with a display or other visual component. As an example, different types of exploration may be easily switched between by orienting the explorer device (100) in different ways relative to the user, causing a change in the configuration of the explorer interface (110) in response to detecting an orientation change via the location service (102). This could include, for example, holding the explorer device (100) flat (e.g., horizontally on its back) with the top of the explorer device (100) directed in a direction of interest, in a "portrait mode" (e.g., vertically with the top of the explorer device (100) pointing upwards) with its back directed in a direction of interest, or in a first or second "landscape mode" (e.g., vertically with the top of the explorer device (100) pointing left or right) with its back directed in a direction of interest. In this manner, a visually impaired person might switch between directed exploration and omnidirectional exploration by orienting the exploration device (100) in the first or the second landscape mode position. These examples and others will be discussed in more detail below.

Figure 2:
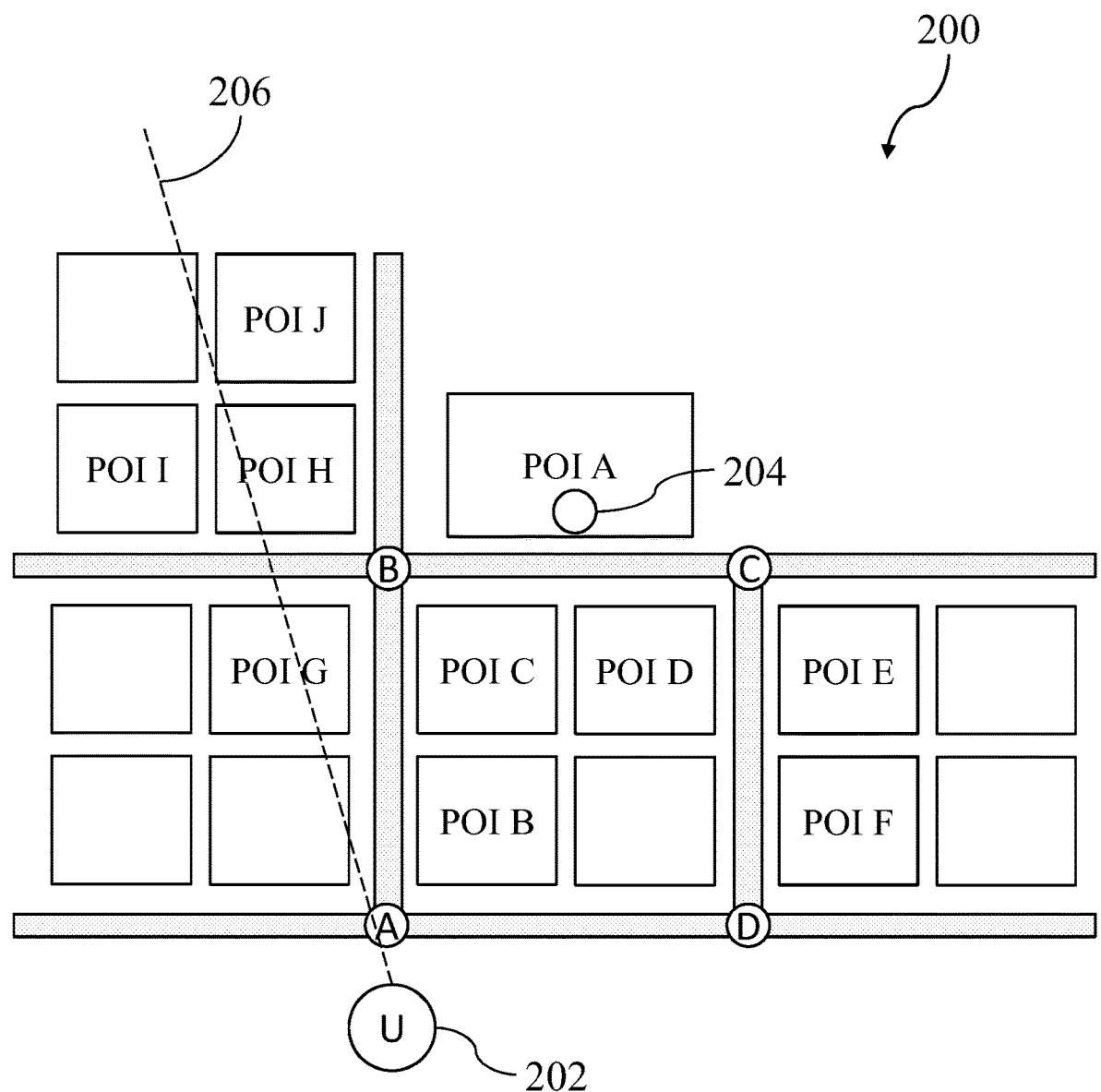
FIG. 2 shows a schematic diagram of an outdoor area that may be navigated with the explorer system of FIG. 1.
Figure 3A:
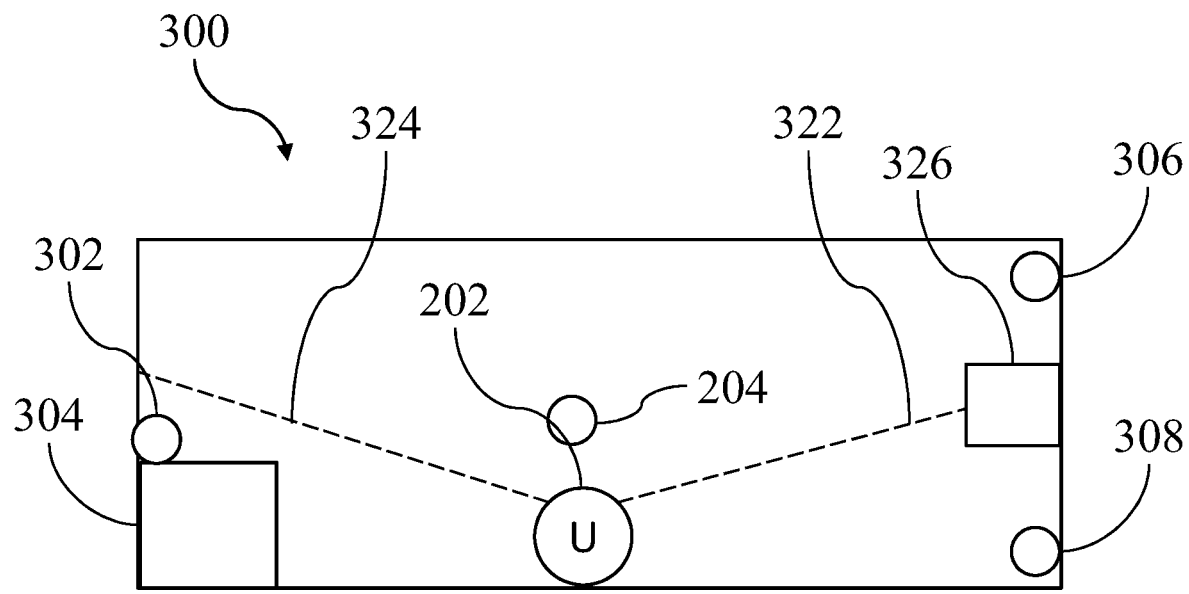
FIG. 3A shows a schematic diagram of a first floor of an indoor area that may be navigated with the explorer system of FIG. 1.
Figure 3B:
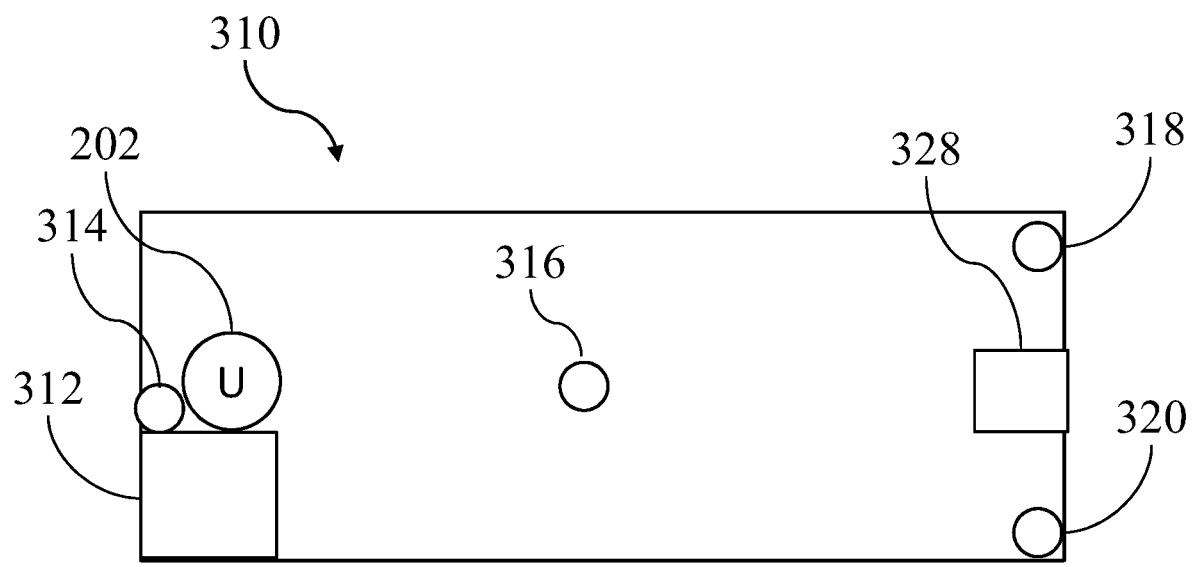
FIG. 3B shows a schematic diagram of a second floor of an indoor area that may be navigated with the explorer system of FIG. 1.

In order to provide a sense of the features and functions of the explorer system (10), FIG. 2 shows a schematic diagram of an outdoor area (200) that may be navigated with the explorer system of FIG. 1, while FIGS. 3A and 3B respectively show a schematic diagram of a first floor (300) and a second floor (310) of an indoor area that may be navigated with the explorer system of FIG. 1. In the outdoor area (200), points of interest or mapped objects are marked on structures as POI A through POI J, while intersections are marked A through D. The starting point of a user (202) is marked as U, and a directional orientation (206) extends from the user (202) across the outdoor area (200). FIGS. 4-9, described below, will make some reference to the exemplary diagrams of FIGS. 2, 3A and 3B to illustrate various exploration features and modes.

Figure 4:
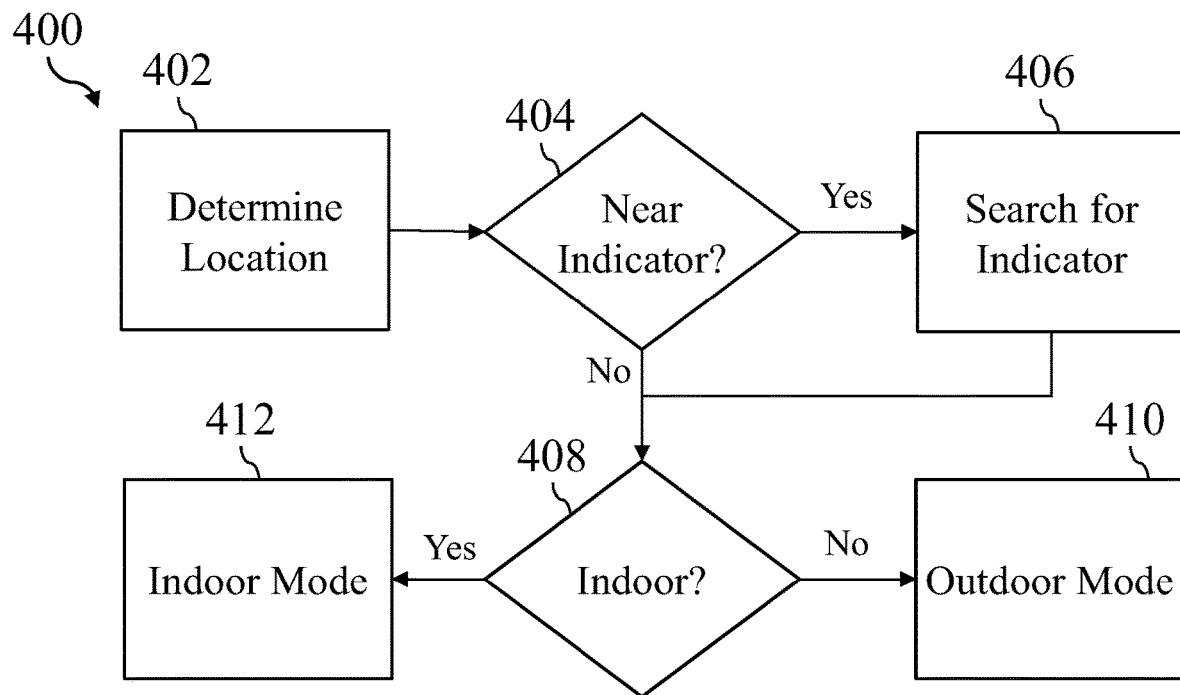
FIG. 4 shows a set of exemplary steps that may be performed to transition between an outdoor area mode and an indoor area mode.

Turning now to FIG. 4, that figure shows a set of exemplary steps (400) that may be performed to determine whether the explorer interface (110) should be in an outdoor mode or an indoor mode, and when it should transition between. When the explorer interface (110) is first activated, such as at the start of a trip through a city or other location, or upon resuming a trip after a break, a location of the explorer device (100) may be determined (402) using the location services (102). This may include, for example, using a GPS receiver to determine the latitude and longitude of the explorer device's (100) current location. With the current location known, the explorer interface (110) may determine whether the current location is near (404) or within a configured distance (e.g., a user configured distance, an arbitrary distance such as 100 feet, or the maximum distance of communication between the indicator monitor (104) and a location indicator (106)) of a location having one or more location indicators (106) installed and configured in the location server (108).

If the current location is near (404) a location having location indicators (106), the explorer interface (110) may begin to search (406) for the one or more location indicators (106). Searching (406) may include enabling the indicator monitor (104) from a disabled or low power state, or changing a configuration of the indicator monitor (104) so that it is actively searching for or receptive of signals from location indicators (106). Where there are no nearby (404) locations having location indicators (106), the indicator monitor (104) may be disabled, placed in a lower power state, or may otherwise be configured to cease searching for location indicators (106), or cease receiving signals from location indicators (106) or other similar indicators. Such a feature may be advantageous, in that it reduces the power consumption and processor time used by the indicator monitor (104) when there are no location indicators (106) nearby, even if there are other indicators or wireless signals within range. Such a feature is especially advantageous for a visually impaired person that is relying upon the explorer device (100) for navigation, as it may increase the longevity of the battery or other power source of the explorer device (100) during the course of a trip and allow greater freedom of exploration.

After determining the status of the indicator monitor (104), the explorer device (100) may then determine (408) whether the device is presently located in an indoor area or an outdoor area. This may be accomplished by, for example, using a location provided by the location services (102) to determine whether the current location is within an outdoor area or within a structure, or by determining whether the indicator monitor (104) is presently communicating with a location indicator (106) that is located within an indoor space, or both. Where the explorer device (100) is outdoors, the explorer interface (110) may be configured (410) to operate in an outdoor mode. Similarly, where the explorer device (100) is indoors, the explorer interface (110) may be configured (412) to operate in an indoor mode.

As an example of the above, with reference to FIG. 2, a location indicator (204) is shown at an entrance of POI A, which may be a large structure such as a museum or retail location. Where the user (202) is located on FIG. 2 (i.e., near intersection A), the explorer interface will determine (402) the location and receive information indicating the user (202) location as shown. At this location, the user is several intersections away from POI A and the location indicator (204), which in most cases will be too great a distance for communication between the indicator monitor (104) and the location indicator (204). Since there is no nearby location indicator, the indicator monitor (104) will be configured conserve power. Next, the explorer interface will determine (408) whether the current location is indoors. This may be determined (408) using the same location as the earlier determination (402), or may be based upon active communication with a location indicator. Since the indicator monitor (104) is inactive in this example, and the location information indicates the user (202) is outdoors, the explorer interface (110) will operate (410) in outdoor mode.

Continuing the example, the user (202) may proceed from intersection A to intersection B while using the explorer device (100) in a directed exploration mode (e.g., holding the explorer device (100) flat and pointing it in the direction for which information is desired, resulting in audio narration of intersections, structures, and other objects in that direction). Upon reaching intersection B, the explorer interface (110) may now, based upon a newly determined (402) location, determine that the location indicator (204) is nearby (404), and will configure the indicator monitor (104) to begin receiving communications from location indicators, although the user may still be outside the range of the location indicator (204).

As the user proceeds from intersection B to intersection C using directed exploration, the location indicator (204) may become within a communicable range with the explorer device (100), and may provide self-identifying information to the explorer device (100) that can be used with information from the location server (108) to indicate a proximity to the entrance to POI A as the user (202) approaches. As a variation on this example, the location indicator (204) may be placed within POI A, and may be configured to self-identify only at short distances that would indicate the user (202) has just entered POI A (202) as opposed to communicating throughout the approach to the entrance. In either case, where the communication with the location indicator (204) or the location information from the location services (102) indicates (408) that the user (202) has entered the building, the explorer interface (110) may begin to operate (412) in the indoor mode.

The differences between indoor mode and outdoor mode will vary by implementation, but as an example may include hardware configuration changes, user input or interface changes, user output changes, and changes to the available datasets that directed exploration and other types of exploration search and provide narration for. A hardware configuration change might include, for example, automatically disabling features of the location service (102) that do not function accurately within structures (e.g., disabling a GPS receiver) in order to further conserve power. User output changes may include, for example, changing the volume of audio narration to increase or reduce volume, providing a haptic feedback or audio alert to indicate a mode switch, or other similar changes.

Input and interface changes may include changing control types or exploration features. For example, in outdoor mode, the explorer interface (110) may be in an intersection mode when the explorer device (100) is held in a landscape mode orientation, and may cause the explorer interface (110) to only provide audio narration related to street intersections in the desired direction (e.g., "$3^{rd}$ and Oak 50 feet, $4^{th}$ and Oak 150 feet, $6^{th}$ and Oak 300 feet . . . "). Since street intersections are less relevant when inside a structure, holding the explorer device (100) in landscape mode while indoors may instead result in audio narration related to a nearby exit from the structure, a nearby restroom, a nearby help desk, or other similar information.

Changes to the available datasets for audio narration may include associating certain objects with an outdoor mode and others with an indoor mode, and then filtering the exploration experience based thereon. For example, when in indoor mode, intersections, crosswalks, business entrances, and location indicators (106) associated with a structure other than the structure the user (202) is currently in may be disregarded when using directional exploration. In this manner, if the user (202) is standing within a structure and directionally exploring mapped objects within that structure, their results may be confined only to objects and mapped objects within that structure, as opposed to receiving information on mapped objects that are outdoors or in a separate structure. Similarly, when in outdoor mode mapped objects within nearby structures may be disregarded, such that directional exploration will provide audio narration of intersections and nearby businesses without providing information on mapped objects within those businesses.

While the explorer interface (110) may confine identified mapped objects based on whether it is in indoor mode or outdoor mode as described above (e.g., confining results to mapped objects within the present structure when indoor mode), the explorer interface (110) may also be configured to only partially filter such results. For example, the explorer interface (110) may be configured to confine mapped object results for indoor mode to any mapped objects within the present structure, as well as bus stops or other mass transit mapped objects outside of the present structure. This may allow a user to identify a nearby bus stop, and then choose an exit from the structure that will place them near that bus stop. Similarly, it may be useful while in outdoor mode to see outdoor mapped objects as well as a subset of indoor mapped objects (e.g., a restroom, device charging station, or Wi-Fi hotspot). Such partially confined search results may be manually configured by a user, or may be configured for or assigned to a particular control type or interface mode.

Figure 5:
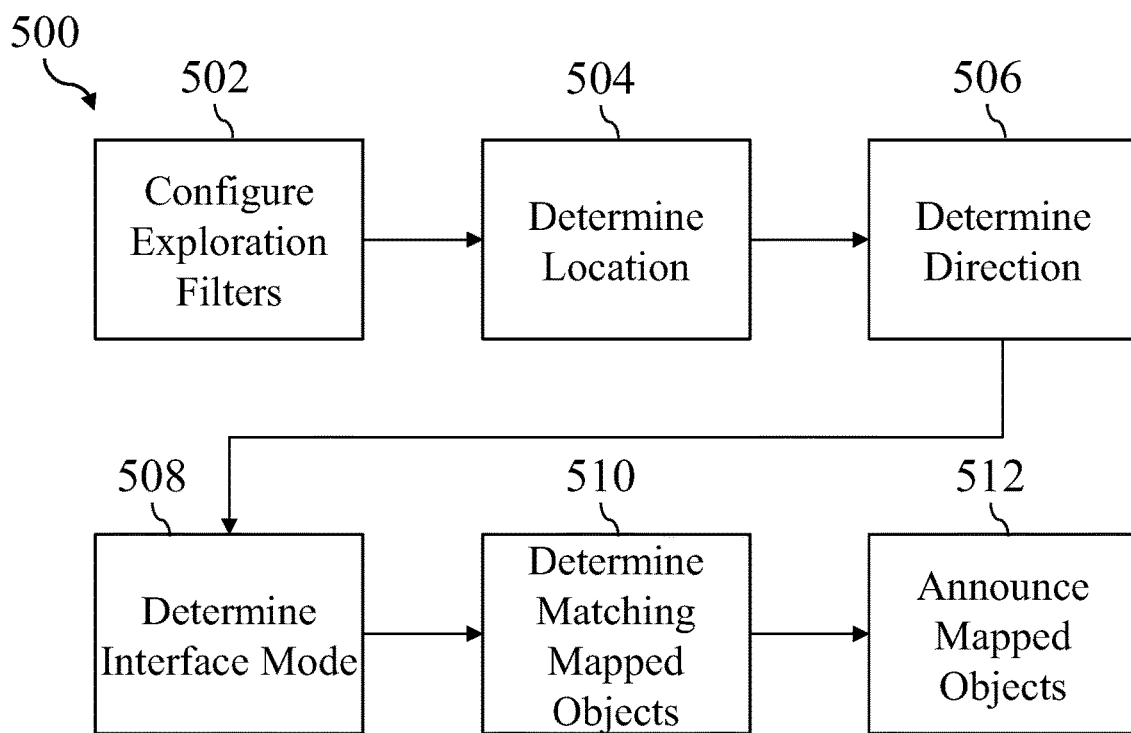
FIG. 5 shows a set of exemplary steps that may be performed to provide navigation assistance while in the outdoor mode.

While there has already been some discussion of directional exploration in various contexts, FIG. 5 shows a set of exemplary steps (500) that may be performed to provide navigation assistance, including directional exploration, while in the outdoor mode. Initially, the explorer interface (110) may be configured (502) with one or more filters for mapped objects that the user is not interested in. This may include, for example only enabling certain types of businesses such as restaurants to be identified during exploration, disabling bus stops or other mass transit related mapped objects where the user prefers to walk, and other filtering and preference options. Configuration may also include configuring a cone width or angular range of directional exploration (e.g., how wide or narrow a search field or cone is in the desired direction), configuring maximum range of directional exploration (e.g., how long is the search field in the desired direction), configuring maximum search depth (e.g., the number of results from the direction that will be narrated, in order from closest to furthest, before stopping), and other configurations that may help a user to limit the amount of audio narration received to only useful and usable amounts.

As another example of a configuration, the explorer interface (110) may be configured (502) to only provide information on businesses and other structures that contain location indicators (106), allowing a user to filter out results for indoor areas that they might have limited ability to navigate due to the lack of location indicators (106). In some implementations, the explorer interface (110) may provide various context driven changes to the mapped object search characteristics described above. For example, some exploration modes might be intended to explore only intersecting streets in a given direction, and may be useful to gain information on intersecting streets that are a mile or further ahead in a given direction. Such an exploration mode might override a globally configured search range limit or search depth limit.

As another example, some configurations that are intended to limit mapped object search results and corresponding narration during directional exploration may be useful to provide a manageable number of relevant results while a visually impaired person is moving through an area at walking speeds. However, the same configurations may not be as useful where the visually impaired person is a passenger in a vehicle such as a car, bus, or subway car.

For example, an exploration distance of around a hundred feet may be desirable while moving through an area at a walking speed of 1-3 mph. Limiting search to the same distance while riding as a passenger in a car at even a moderate speed of 30 mph may result in the identified mapped objects in a direction being bypassed and no longer relevant before the audio narration of their presence ends. In such a case, the explorer interface (110) may be configured to manually (e.g., in response to a user input) or automatically (e.g., in response to information from the location services (102) indicating a speed that exceeds walking speed) enter a passenger exploration mode. In such a passenger exploration mode, directional exploration could function normally, except that one or more of the maximum distance, width, or depth of search results that are identified and announced could be increased to account for the increased speed of travel.

This may be advantageous for a user, in that the explorer interface (110) could automatically switch to passenger mode when transit beyond walking speeds begins, and could allow the visually impaired person to explore their surroundings at a greater distance and depth. As a result, they may discover a mapped object or other destination more quickly and at a greater distance, which may give them more time to communicate with a driver of a vehicle their intent to disembark from the vehicle before the desired mapped object or destination is passed by.

Once configured (502), the explorer interface (110) may then determine (504) a location of the explorer device (100) and determine (506) a direction of exploration. As has been discussed, location and direction may be determined in various ways using the location service (102), including using GPS positioning and a compass, for example. The explorer interface (110) may also determine (508) an interface mode in implementations where different control types are supported. As has been discussed, this may include determining the orientation of the explorer device (100) (e.g., flat, portrait mode, landscape mode), and then identifying a set of features or controls associated with that orientation.

Based upon the configuration, location, direction, and interface mode, the explorer interface (110) may then determine (510) a set of matching mapped objects, which may then be announced (512) via an audio device of the explorer device (100). To provide several examples, with reference to FIG. 2, where the user (202) is using directed exploration and is directed at the orientation (206), the matching mapped objects may be determined (510) to include intersection A, street B-C, and POI G, H, J and I, each of which may then be announced by the explorer device (100) from nearest to furthest. In the same example, if directional exploration had been configured to provide a narrow search angle, POI I may be excluded from the matching results and announcement. Where the search distance had been configured to provide a shorter search distance, POI J may be excluded from the matching results. Where the search depth had been configured to a depth of four, the matching results may only include intersection A, POI G, street B-C, and POI H, while excluding deeper results.

Figure 6:
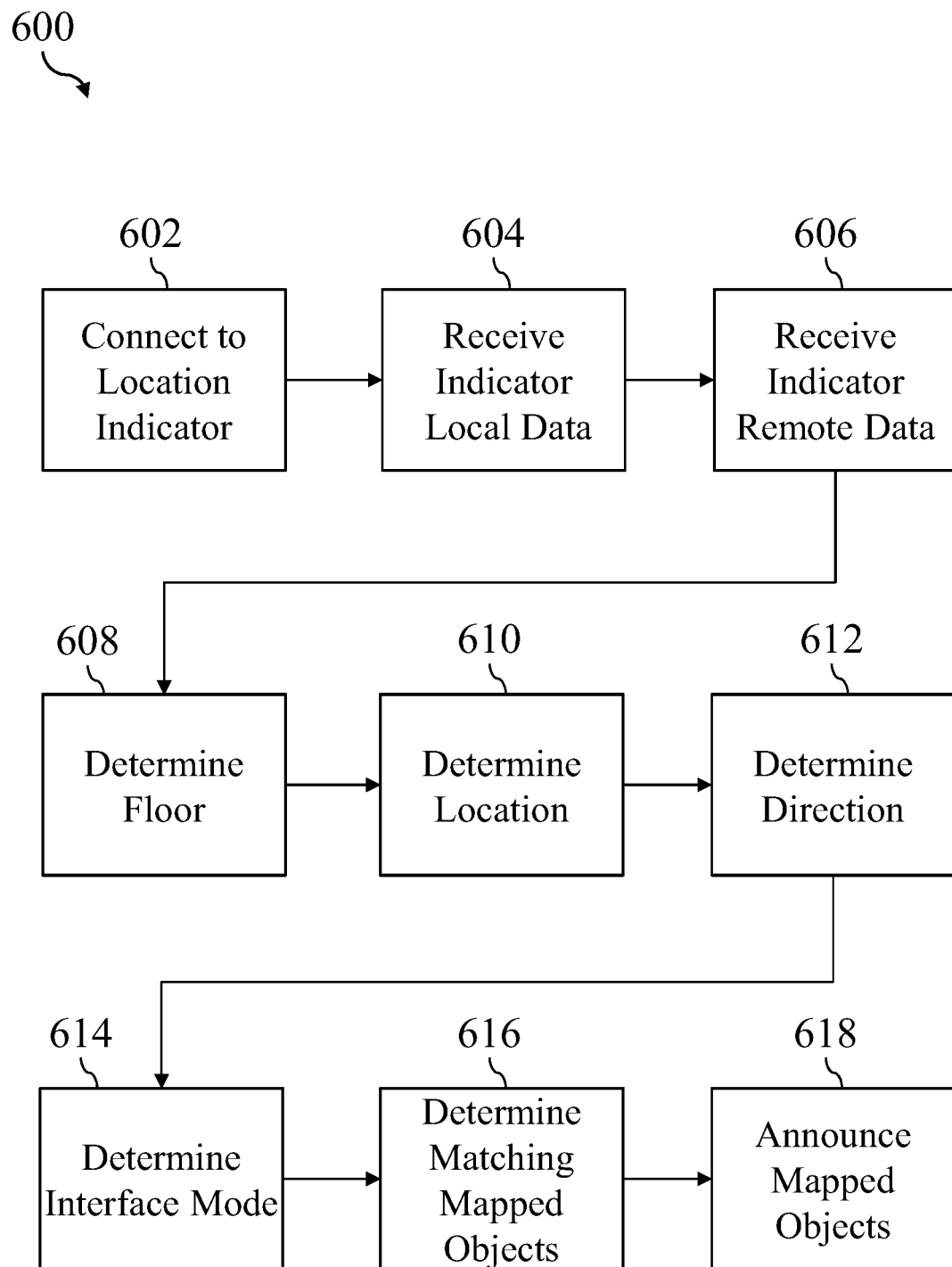
FIG. 6 shows a set of exemplary steps that may be performed to provide navigation assistance while in the indoor mode.

In the same example, differing control types may also provide different matching POI and corresponding announcements. For example, in one control type (e.g., landscape one) only information on streets may be provided, including descriptions of intersection A and street B-C. In another control type (e.g., flat mode), only information on structures may be provided, including descriptions of POI G, H, I, and J. In yet another control type (e.g., landscape two), only information on the nearest POI may be provided, including descriptions of intersection A. In yet another control type (e.g., portrait mode), the nearest POI in all directions, up to a maximum depth of five may be provided, including descriptions of intersection A, POI B, C, D, and intersection B. These control mode results are exemplary only, and it should be understood that various other control types and corresponding results are possible As has been discussed in the context of FIG. 4, when a user transitions from an outdoor area to an indoor area during directional exploration the explorer interface (110) may provide a different set of features compared to those described in FIG. 5. Exploration using indoor mode will ideally utilize one or more location indicators (106) distributed across an indoor environment (e.g., placed near and associated with a particular POI like a water fountain or restroom, or spread throughout an area and used in combination to provide multi-indicator triangulation). However, it should also be understood that in at least some cases the location services (102) may be able to provide an indoor position without any location indicators, such as where GPS, Wi-Fi positioning, or other location service features function within a particular indoor environment. In cases where location indicators (106) are unavailable, directional exploration may function similarly to the steps described in the context of FIG. 5.

Where an indoor environment has one or more location indicators (106) available, FIG. 6 shows a set of exemplary steps (600) that may be performed to provide navigation assistance and directional exploration using feedback from location indicators (106). As an explorer device (100) moves about an indoor area while in the indoor mode, one or more location indicators may be within range of the indicator monitor (104), and the explorer device (100) may connect (602) with one or more of the nearby location indicators and receive (604) a set of local indicator data from each. Communication with the location indicators may be bi-directional or uni-directional depending upon a particular implementation. Received (604) local data will also vary, but may include information such as a latitude and longitude at which the location indicator is placed, a unique identifier associated with that particular location indicator, a status indicator that indicates whether that particular location indicator is indoors or outdoors, a battery status for that location indicator, which the explorer interface (110) may provide to the explorer server (112) or another recipient to provide alerts when a battery needs to be charged or replaced, a distance from the location indicator to the communicating explorer device (100), and other information. Data present on the location indicator may be statically configured at the time of install, and may be updated from time to time.

The explorer device (100) may also receive (606) a set of remote indicator data. Received (606) remote indicator data will vary, but may include information from the location server (108) as has been described above, which may include information such as descriptions and locations of mapped objects, and descriptions and locations of location indicators. The remote indicator data may be received (606) in real time (e.g., such as by communication between the explorer device and the location server (108) when indoor mode is entered) or may be received (606) intermittently (e.g., such as where the remote indicator data is packaged into an application that is installed on the explorer device (100), or where updated remote indicator data is pushed to the explorer device (100) based on an update schedule rather than on demand).

Using one or more of the local and remote indicator data, the explorer device (100) may determine (608) a floor or level of a structure at which the explorer device (100) is located, and announce such information to the user. This is advantageous, in that other types of positioning (e.g., GPS positioning) can provide a two dimensional position on a map, but cannot determine what level or floor of a structure the explorer device (100) is located on. Determining (608) the floor that a visually impaired person is located on is useful because it allows the explorer interface (110) to provide an accurate position to the user, and because it allows the explorer interface (110) to accurately represent nearby mapped objects (e.g., if a restroom is located on a first level of a two-level structure, the current level must be known in order to directionally locate the restroom), and to filter nearby mapped objects during exploration (e.g., if a user is on a first level of a two-level structure, directional exploration can be used to identify mapped objects on the first level while filtering out and disregarding mapped objects on the second level).

Received (604) local data may be used to determine (610) the explorer device's (100) location and distance from a particular location indicator, or a location within a particular structure, or both. For example, in a case of a single location indicator with a known static position (e.g., latitude and longitude), the explorer device (100) may receive information indicating the distance between the location indicator and the explorer device (100) that is refreshed in near real-time. Such information could be used with information from an accelerometer or compass feature of the explorer device (100) to determine (612) a direction and speed of movement of the explorer device (100), which may be used with a set of changing distance measurements from a location indicator to approximate a position of the explorer device (100) relative to the location indicator (e.g., if the explorer device is moving in a first direction at 0.5 meter per second, and information from the location indicator shows the distance between the location indicator and the explorer device (100) decreasing by 0.5 meter per second, it can be determined that the first direction is the direction of the location indicator). With the position of the explorer device (100) known relative to the location indicator, the explorer device's (100) position with the indoor area can also be approximated as a function of the static latitude and longitude provided by or associated with the location indicator.

The above example may also be applied where two location indicators are available, and may use distance information from each location indicator in combination to more accurately determine the direction and location of movement, and corresponding position within the indoor structure. In the case of three or more location indicators, triangulation and trilateration techniques may be used to determine the explorer device's (100) position without reliance upon additional inputs, such as directional velocity from the accelerometer.

After determining (610) the location and determining (612) the direction of exploration, the explorer interface (110) may also determine (614) the current interface mode that a user is using for the explorer device (100) (e.g., the control type, input type, or interface type the user has configured or selected, such as by orienting the explorer device (100) in a flat, portrait, or landscape mode, as has been described in the context of FIG. 5 and determining (508) the interface mode). The explorer interface (110) may then determine (616) any matching mapped objects for the directional exploration based upon information on mapped objects from the location server (108), and then announce (618) the identified mapped objects for that direction. Similar to the examples described in the context of FIG. 5 and outdoor directional exploration, this allows the user to directionally explore the indoor environment and, based upon the determined floor (608), location (610), and direction (612) of the user, receive audio narration via the announced (618) mapped objects. As with outdoor exploration, indoor exploration according to the steps of FIG. 6 may also be configured (e.g., as in the context of configuring (502) the explorer interface (110)) to limit indoor exploration results by distance of search, width of search, depth of search, and other options.

To provide an example of the above, with reference to FIGS. 3A and 3B, as the user (202) steps into the first floor (300) the explorer interface (110) may enter the indoor mode and connect (602) to one or more nearby location indicators. In this example, the explorer interface (110) may connect (602) to three location indicators (204, 306, 308), receive (604) local indicator data (e.g., a unique identifier, a latitude and longitude, a connection distance) from each, and use the local indicator data with received (606) remote indicator data to make several determinations.

This may include determining (608) that the user (202) is on the first floor (300) based upon an association of one or more of the three location indicators (204, 306, 308) with the first floor (300) in the set of remote indicator data. In some implementations, a triangulation of the three location indicators (204, 306, 308) may be performed to determine a current floor instead of or in addition to other methods of determining the current floor. This may also include determining (610) that the user (202) is at the location shown in FIG. 3A based upon a triangulation of the three location indicators (204, 306, 308), and further, determining (610) the user's latitudinal and longitudinal position based upon the known static positions of each location indicator and the triangulation of the explorer device (100) relative to each location indicator. This may also include determining (612) that the user (202) is directionally exploring in the direction of an orientation (308), represented by a dotted line, based upon the explorer device's (100) accelerometer, compass, or another feature.

In this example, the explorer interface (110) would, based on the floor, location, direction, and any interface mode, search an indoor mapped object dataset (e.g., such as that available from the location server (108)) to find any mapped objects matching the exploration criteria. In this case, a restroom (326) may be identified as a match (616) within the indoor mapped object dataset as being on the identified floor (e.g., on the first floor (300), excluding the restroom (328) on the second floor (310) from the results), and within the direction of the location (e.g., following along or within a searchable cone or width of the orientation (322)). The explorer interface (110) may then announce (618) the restroom (326), which may include describing it as a restroom, describing any relevant notes or details associated with it in the mapped object dataset from the location server (108), such as whether it is handicap accessible or unisex, and describing the distance from the user (202) location to the restroom (326) location.

While the above example describes confining announced results to only mapped objects located on the current floor, some implementations of the explorer interface (110) may allow a user to explore mapped objects on other floors by directionally exploring upwards (e.g., pointing the explorer device upwards in addition to directionally) or downwards (e.g., pointing the explorer device downwards in addition to directionally). In such an implementation, exploring upwards and directionally rotating may result in exploration of mapped objects on the floor immediately above the current floor, while exploring downwards and rotating may result in exploration of mapped objects on the floor immediately below the current floor.

Continuing the above example, if the user (202) then directionally explores in the direction of the orientation (324), shown as a dotted line, the above steps may be repeated in order to announce (618) the location of an elevator (304). The user (202) may proceed in the direction of the elevator, leaving the range of the location indicators (306, 308) and entering the range of the location indicator (302). In this case, the explorer interface (110) may use information from the newly connected location indicator (312), the location indicator (204), or both, using a single indicator or dual indicator locating method as has been described, to determine (610) the location of the user (202) without requiring triangulation.

In some implementations of the explorer system (10), the location indicator (302) may have additional features to assist the user (202) in orienting themselves towards the location indicator (302) and the nearby elevator (304). For example, in some implementations the location indicator (302) may also include an audio device capable of emitting a voice or other signal tone in response to interactions with the explorer interface (110). This could include providing an intermittent beep whenever the indicator monitor (104) is in ongoing communication with the location indicator (302), providing a beep in response to a signal or request from the indicator monitor (104) (e.g., such as where the user (202) presses a button of the explorer device (100), shakes the explorer device (100) to generate an accelerometer dataset indicating a purposeful shake, or provides other inputs), or providing a first tone when the user (202) is substantially directly approaching the location indicator (302) and a differing tone when the user (202) is either indirectly approaching the location indicator (302) or growing further away from the location indicator (302).

As another example, which may be implemented independently or in combination with the above, the location indicator (302) may be integrated into a sign, placard, or other object which provides information to the visually impaired according to a specified standard or set of guidance. This may include, for example, signage following any type of standard or requirement such as the Americans with Disabilities Act requirements for size, placement, braille text, and other characteristics. In this manner, the user (202) may proceed to the location indicator (302) and then read a braille description present on the integrated signage to verify that they have arrived at the elevator (304).

Upon exiting via the elevator (312) on the second floor (310), the explorer device (100) may connect (602) to two location indicators (314, 316) and update the floor, location, and direction of directional exploration, resulting in the bathroom (326) no longer being announced, and the second floor bathroom (328) being announced instead. As the user (202) moves throughout the second floor (310), other location indicators (318, 320) may also connect and provide additional information and triangulation features. In some cases, a location indicator such as the location indicator (318) may itself be placed proximately to and directly associated with a mapped object such as a water fountain, fire escape route, or other feature, rather than being placed on a ceiling or wall and configured only to provide information for triangulation. In this manner, the explorer interface (110) may use information from the location indicator (318) for both triangulation, and for direct guidance where desired (e.g., by providing an audible tone from the location indicator (318), by providing ongoing distance updates to the location indicator (318) as the user approaches).

Figure 7:
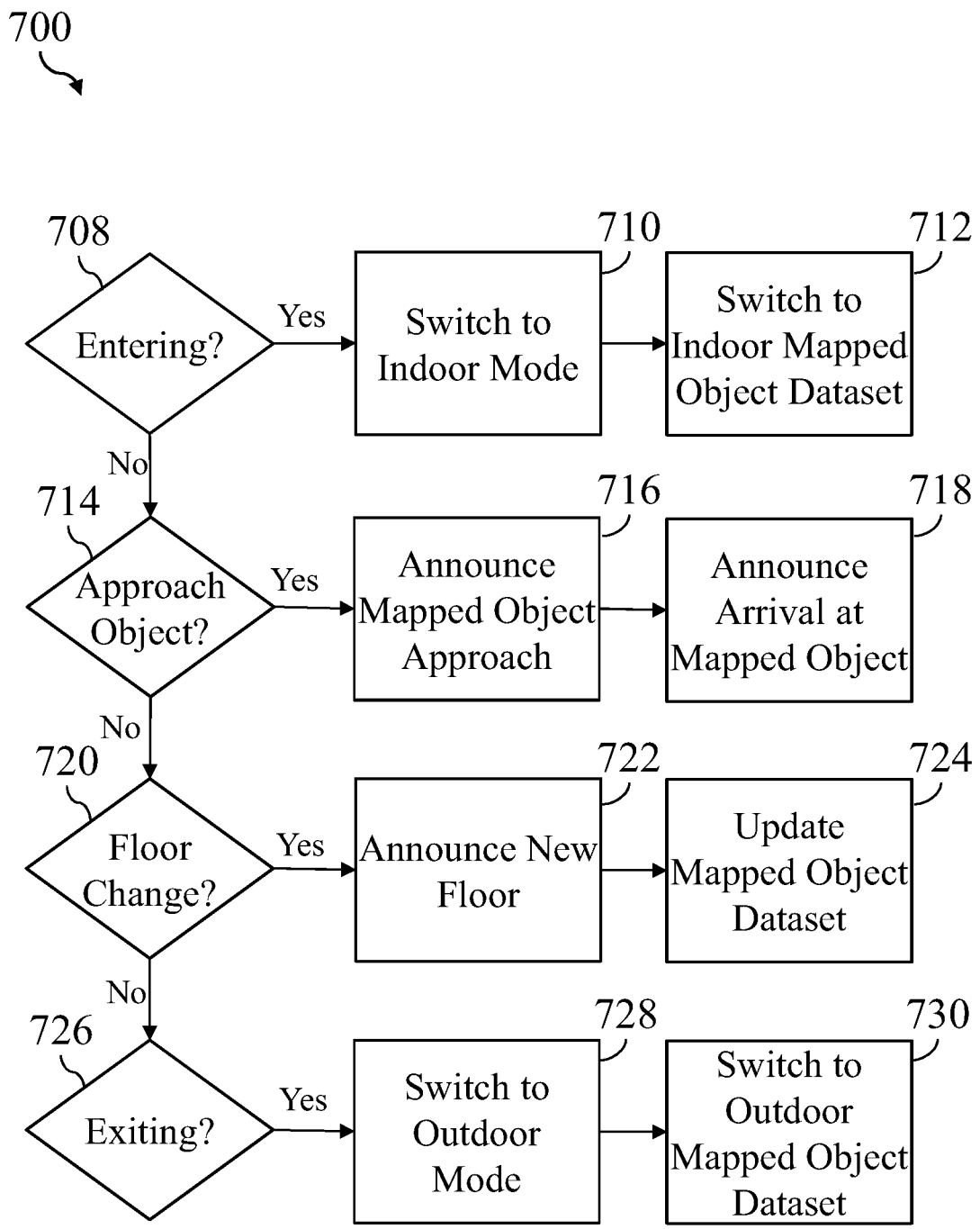
FIG. 7 shows a set of exemplary steps that may be performed to provide location indicator based guidance while in the indoor mode.

FIG. 7 shows a set of exemplary steps (700) that may be performed to provide location indicator based guidance while in the indoor mode, as has been discussed in some detail in the context of FIG. 6. During exploration of an indoor environment with available location indicators, the explorer interface (110) may perform certain actions automatically as a result of connection to one or more location indicators, or in response to a user input or action, in addition to providing directed exploration and other described features.

For example, when the explorer interface (110) determines (708) that the explorer device (100) is entering an indoor area based upon communication with a location indicator, it may switch (710) to indoor mode from outdoor mode, which may result in changes to hardware and software configurations as has been described, and may switch (712) to an indoor mapped object dataset, resulting in some or all mapped objects that are outside of or otherwise not associated with the current indoor environment being filtered from exploration results. Switching (710) to indoor mode may also include a user feedback such as a haptic vibration or audio announcement indicating that the explorer interface (110) is now in indoor mode, announcing the name or description of the indoor environment the user is within, and announcing a level of a structure that the user is currently within.

When the explorer interface (110) determines that the explorer device (100) is approaching (714) a mapped object that has been selected by the user as a destination mapped object, or that the explorer interface (110) has otherwise determined that the user is approaching as a destination, the explorer interface (110) may announce (716) the approach to the mapped object at various intervals (e.g., time intervals or distance intervals) and may cause a location indicator associated with the mapped object to emit a tone or voice as has been described. Further, when the explorer interface (110) determines that the user has arrived at a mapped object, the explorer interface (110) may announce (718) that the user has arrived at the mapped object using audio narration, or may cause a location indicator associated with the mapped object to emit a tone or voice.

When the explorer interface (110) determines that the explorer device (100) has transitioned (720) from one level of a structure to another, the explorer interface (110) may announce (722) the level of the new floor, and update (724) the mapped object dataset to include mapped objects from the current level, and exclude mapped objects from other levels.

When the explorer interface (110) determines that the explorer device (100) has exited (726) the current indoor structure, the explorer interface (110) may switch (728) to outdoor mode, which may result in hardware and software configuration changes as has been described, and may switch (730) to an outdoor mapped object dataset, causing mapped objects from within structures to be excluded from directional exploration results.

Figure 8:
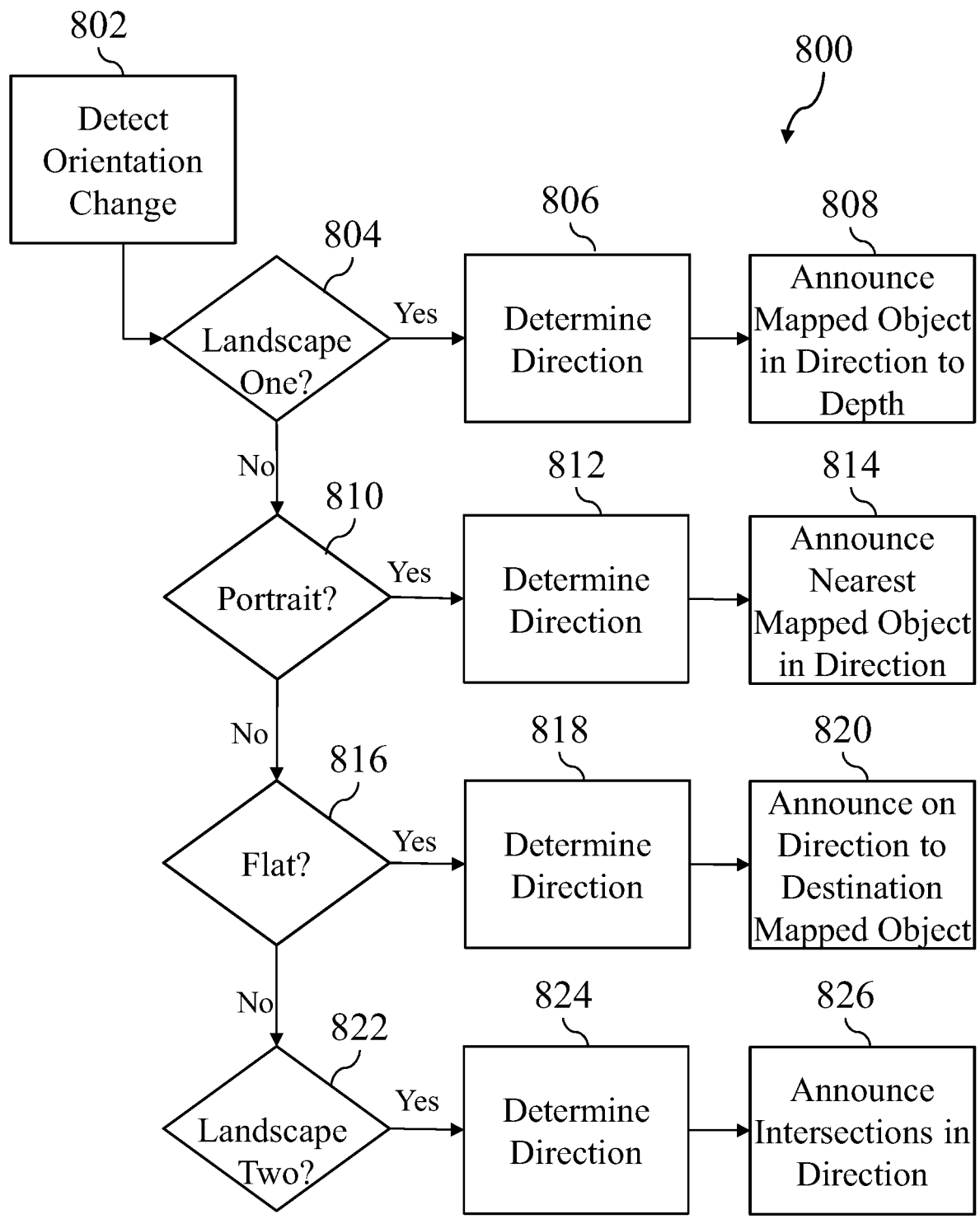
FIG. 8 shows a set of exemplary steps that may be performed to change interface modes.

While using the explorer device's (100) orientation to change between different control, input, and interface modes has been described in some detail above, FIG. 8 shows a set of exemplary steps (800) that may be performed to change interface modes based upon a detected (802) orientation change. For example, where the orientation change is to a first landscape mode (804), the explorer interface (110) may determine (806) the direction of exploration by using a compass feature to determine the direction that the rear (e.g., where the explorer device (100) is a smartphone, the rear portion of the phone opposite the glass touch screen) of the explorer device (100) is facing. The explorer interface (110) may then provide directional exploration results for that direction, including announcing (808) all mapped objects (e.g., all outdoor mapped objects including streets, intersections, and structures) up to the maximum configured depth of search.

Where the orientation change is a portrait mode (810), the explorer interface (110) may determine (806) the direction of exploration by using a compass feature to determine the direction that the rear of the explorer device (100) is facing. The explorer interface (110) may then provide directional exploration results for that direction, including announcing (814) only the nearest mapped objects in that direction, which may be advantageous where a user wishes to remain in place and quickly explore only the closest mapped objects in a circle or arc around their present location, rather than exploring a number of mapped objects in each direction.

Where the orientation change is a flat mode (816), the explorer interface (110) may determine (818) the direction as the direction in which the top (e.g., where the explorer device (100) is a smartphone, the narrow edge at the top of the device where a headphone jack is sometimes located) of the explorer device (100) is pointed. The explorer interface (110) may then provide directional exploration results for that direction that only include a selected destination mapped object, and exclude all other mapped objects. In this manner, a user may stand in place with the explorer device (100) in a flat mode, and point in various directions, with the explorer device only providing narrated exploration results when the destination mapped object is within the explored direction. This may be useful where a user is navigating to a destination while also exploring mapped objects located along their route, as a user may wish to regularly orient the explorer device (100) between the portrait mode (e.g., exploring the nearest mapped object in a direction) and the flat mode (e.g., exploring for only the destination mapped object). This may result in an exploration experience similar to that of a sighted person, where the user may regularly orient themselves towards a final destination in one mode, while using a second mode to explore and discover nearby mapped objects, without having to stop and manually change software configurations, search settings, or other settings.

Where the orientation change is a second landscape mode (822), the explorer interface (110) may determine the direction as the direction that the rear of the explorer device (100) points, and may provide directional exploration results in that direction that only include intersections. This may be advantageous in that it provides a reduced set of information that is still very relevant for spatially orienting oneself within a larger context of a city or other area. In such an intersection exploration mode the configured constraints for distance, depth, and other characteristics may be modified, such that a user may stand in place and explore in a desired direction, learning about each set of intersecting streets in that direction to a distance or depth that they desire.

The above interface types are exemplary only, and it should be understood that other interface types, orientation types, and combinations thereof exist and will be apparent to one of ordinary skill in the art in light of this disclosure. For example, any reference to a particular functionality in "portrait mode" may also be implemented for "landscape mode" or other modes, and vice versa. In particular, the examples of FIG. 8 are configured towards outdoor exploration, and so indoor exploration modes may have different combinations of features and search results (e.g., such as replacing and intersection search mode with an elevator, stair, and exit search mode).

Figure 9:
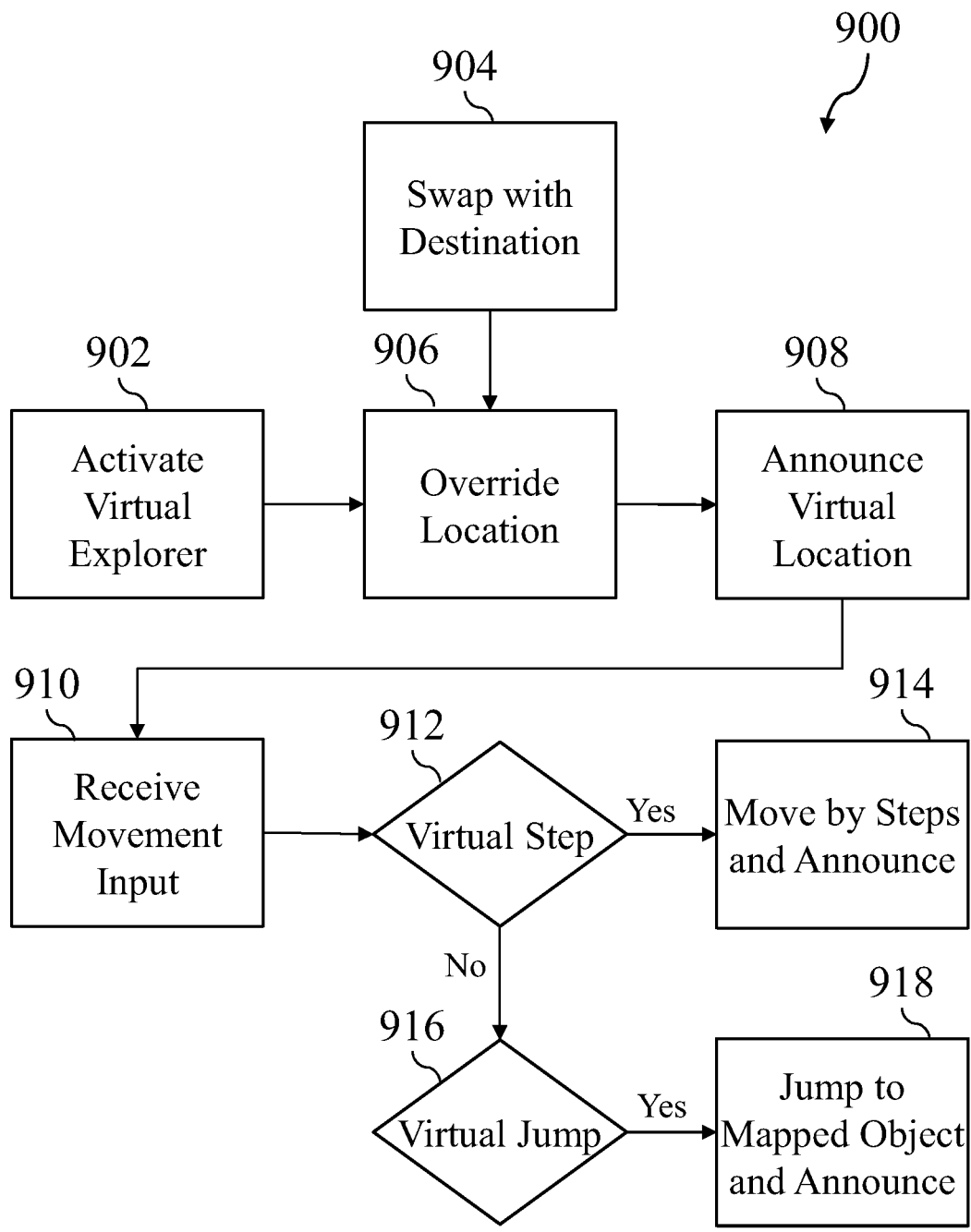
FIG. 9 shows a set of exemplary steps that may be performed to provide a virtual explorer.

In some implementations, the explorer system (10) may support additional features beyond those already described. For example, FIG. 9 shows a set of exemplary steps that may be performed to provide a virtual exploration mode that may be accessed (902) via the explorer interface (110). The virtual exploration mode allows a user of the explorer device to simulate exploration in a desired location, and may be useful for virtually visiting and directionally exploring an indoor or outdoor location that they are planning to visit prior to beginning such a trip, or while taking a break from directional exploration during a current trip. When virtual exploration is activated, the user may provide a location that they wish to begin virtual exploration at (e.g., an interior of a structure, an intersection in a city, a city park, or other location). The explorer interface (110) will then override (906) location results that are provided by the location services (102) with virtual location results matching the selected location, and may then begin to announce (908) audio narration as if the user were physically present at the virtual location.

During virtual exploration, the user may use directional exploration as has been described herein (e.g., pointing and orienting the explorer device (100)) in order to explore and receive narration on mapped objects virtually located in the desired direction. The explorer interface (110) may also receive (910) movement inputs from the user for traversing the virtual environment. Movement inputs may be received based upon the user's interactions with any appropriate user input, and may include voice inputs, hardware key inputs, software key or touchscreen key inputs, and other inputs.

For example, in one implementation the explorer device (100) may include a touchscreen display, and may be configured such that a touch input to an upper half of the touchscreen causes the user to virtually move forward, while a touch input to the lower half of the touchscreen causes the user to virtually move backwards within the virtual environment, simulating the user walking forward in the direction that they are exploring, or moving backwards away from the direction they are exploring.

The explorer interface (110) may also be configured to recognize different types of movement input. For example, some movement inputs may be determined (912) to be a virtual step, while other movement inputs might be determined (916) to be a virtual jump. Virtual step movement may be result in a steady traversal through the virtual environment that approximates the walking speed of a general user (e.g., 1-3 miles per hour), or the walking speed of a particular user (e.g., as may be manually configured, or as may be automatically configured by placing the explorer interface (110) into a walk speed training mode that tracks a particular user's speed as they walk and uses that information to configure virtual walk speed). While moving (914) through a virtual environment with virtual steps, the explorer interface (110) may provide a normal directional exploration interface as has been described, and may also provide additional audio signals or cues associated with the virtual steps, such as a cadence tone to indicate the virtual movement.

Virtual jump movement may result in an accelerated movement through the virtual environment, such as an immediate jump to a destination mapped object, an immediate jump to the nearest mapped object in the current direction, an immediate jump to the most recently announced mapped object, or an immediate jump to the next intersection of streets in the current direction. When the virtual jump occurs, the explorer interface (110) may jump (918) to the intended location and announce the location, which may include announcing a description of the location as well as the distance of the jump (e.g., "You have arrived at $3^{rd}$ and Oak, 300 feet from your previous location"). In this manner, the user may quickly and virtually traverse through a city or other location, experience and gaining a spatial sense of the streets and mapped objects that are located along a potential future route. The explorer device (100) may be configured to differentiate between virtual steps and virtual jumps based upon characteristics of the input. For example, a finger tap, or steady finger hold on a segment of a touchscreen may cause a virtual step forward or backward, while a double finger tap on a segment may cause a virtual jump forward or backward.

In some implementations of virtual exploration, a user may wish to virtually explore some aspects of their surroundings during a current trip. For example, where a user may be currently traveling and using directional exploration while navigating towards a destination point, the user may find it helpful to look for mapped objects such as intersections or other landmarks that are proximate to their destination point, such that the user may recognize those landmarks as they near their destination. In some cases, directional exploration from their current location may not be ideal for learning about landmarks proximate to their destination, whether due to a configuration limiting the range or depth of such exploration. In such cases, a user may instead use virtual exploration to quickly swap (904) their current location with a virtual location at their destination, which would allow them to briefly simulate standing at their destination looking back towards their current location. In this manner, the user might directionally explore from the virtual location of the destination until they have an understanding of its surrounding, and then may exit the virtual exploration and return to real-world directional exploration. Such a virtual exploration feature may be configured to activate based upon a simple input to the explorer device (100), such as an accelerometer input to the explorer device (100) (e.g., a shaking motion) or a voice command.

In some implementations the explorer interface (110) may be configured to present a minimal amount of information and options via a touchscreen display of the device during uses such as exploration mode, as displayed information may be of limited or no value to a visually impaired person. Further, in some cases, providing large amounts of text information via the display may be counterproductive, such as where the explorer interface (110) provides features for voice narration of text directly from the display, or where the explorer device (100) includes or is configured to operate with a braille display. For example, in some cases, the explorer device (100) may be placed in communication with a handheld, mobile braille display via a wireless (e.g., Bluetooth) or wired (e.g., USB) connection. The braille display may receive signals from the explorer device (100) matching text displayed by the explorer device (100), and may mechanically raise and lower sets of surface features, such as groupings of small tactile nodes, to produce braille corresponding to the text.

In such a case, providing the most relevant and most concise information to the braille display may be desirable. To provide such functionality, the explorer interface (110) may be manually configured to provide reduced levels of text display when in exploration mode (e.g., configurations and settings menus may be hidden, other menus or text may be shortened and abbreviated). Further, such configuration changes may also be made by the explorer interface (110) automatically when a braille display is detected as being connected to the explorer device (100). In such a case, the explorer device (100) may determine the capabilities of the connected braille display (e.g., how many braille characters it may display at once), and then may abbreviate, remove, or otherwise reduce the amount of text displayed by the explorer interface (110) at any one time such that it may be displayed by a single line of the braille display.

Some implementations of the explorer system (10) may include features and methods to improve the accuracy and results of trilateration and other positioning techniques when using location indicators. For example, in some embodiments, a smoothing function may be applied to reduce jitter in signals received from location indicators. Similarly, in some embodiments, there may be functionality to identify when a trilateration result would place the explorer device (100) in an impossible location (e.g., where information received from nearby location indicators indicates that the user is six feet from each location indicator, but the remote indicator data indicates that the location indicators are eighteen feet apart) and, in that case, the explorer interface (110), indicator monitor (104), or location service (102) may be configured to gradually recalibrate its distance determinations (e.g., by slowly increasing the perceived distance from the beacons with the strongest signals) until it no longer believes the user to be in an impossible location.

Further variations on, and features for, the inventors' technology will be immediately apparent to, and could be practiced without undue experimentation by, those of ordinary skill in the art in light of this disclosure. Accordingly, instead of limiting the protection accorded by this document, or by any document which is related to this document, to the material explicitly disclosed herein, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "configured" should be understood to mean that the thing "configured" is adapted, designed or modified for a specific purpose. An example of "configuring" in the context of computers is to provide a computer with specific data (which may include instructions) which can be used in performing the specific acts the computer is being "configured" to do. For example, installing Microsoft® WORD on a computer "configures" that computer to function as a word processor, which it does by using the instructions for Microsoft WORD in combination with other inputs, such as an operating system, and various peripherals (e.g., a keyboard, monitor, etc).

When used in the claims, "determining" should be understood to refer to generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims, a "means for providing directional exploration of an indoor environment via the audio device" should be understood as a limitation set forth in the form of a means for performing a specified function as provided for in the sixth paragraph of 35 U.S.C. § 112 in which the specified function is "providing directional exploration of an indoor environment via the audio device" and the corresponding structure is a system having physical components such as the processor described in the context of the explorer device (100), where the processor is programmed to provide an exploration interface with tools and features that allow for audio narration of directed exploration (examples provided in FIGS. 4 and 6-9, and described in the text associated with those figures).

When used in the claims, a "set" should be understood to refer to a collection containing zero or more objects of the type that it refers to. So, for example, a "set of integers" describes an object configured to contain an integer value, which includes an object that contains multiple integer values, an object that contains only a single integer value, and an object that contains no integer value whatsoever.

The invention claimed is:

1. An explorer device comprising:
   (a) a location service operable to provide information indicating a relative orientation of the explorer device;
   (b) an indicator monitor operable to wirelessly receive information from one or more location indicators when they are within range of the indicator monitor;
   (c) an audio device;
   (d) a processor configured to, when the explorer device is in an indoor location:
      (i) determine a direction that the explorer device is directed in based upon a set of direction data from the location service;
      (ii) receive a set of local indicator data from each of a set of location indicators via the indicator monitor;
      (iii) determine a current location of the explorer device and a level of an indoor structure that the explorer device is at based upon:
         (A) the set of local indicator data of each of the set of location indicators; and
         (B) a set of remote indicator data;
      (iv) identify a set of mapped objects within the set of remote indicator data based on the direction, the current location, and the level, wherein each of the set of mapped objects corresponds to and describes a physical object or a physical location; and
      (v) announce each of the set of mapped objects via the audio device.

2. The explorer device of claim 1, wherein:
   (a) the indicator monitor comprises a wireless Bluetooth transceiver;
   (b) the set of location indicators comprises one or more location indicators;
   (c) the set of remote indicator data is stored on a memory of the explorer device;
   (d) each set of local indicator data comprises a unique indicator identifier of the location indicator from which it is received;
   (e) the current location of the explorer device comprises a latitude and a longitude; and
   (f) the set of remote indicator data comprises a latitude and a longitude for each of the set of mapped objects and each of the set of location indicators.

3. The explorer device of claim 1, wherein the set of location indicators comprises at least three location indicators, wherein the processor is further configured to, when determining the current location of the explorer device and the level of the indoor structure:
   (a) determine a unique identifier for each of the set of location indicators based upon the set of local indicator data for each of the set of location indicators;
   (b) using the set of remote indicator data and the unique identifier for each of the set of location indicators:
      (i) determine a latitude and a longitude associated with each of the set of location indicators; and
      (ii) determine the level based upon an association with at least one of the set of location indicators;
   (c) determine a distance between the explorer device and each of the set of location indicators based on the set of local indicator data for each of the set of location indicators; and
   (d) determine the location of the explorer device based upon a trilateration of the distance between the explorer device and each of the set of location indicators and the latitude and longitude for at least one of the set of location indicators.

4. The explorer device of claim 1, wherein the processor is configured to, when identifying the set of mapped objects, select each mapped object from the set of remote indicator data that:
    (a) is within an area that is based upon the current location and the direction; and
    (b) is associated with the level.

5. The explorer device of claim 4, wherein the processor is further configured to exclude from the set of mapped objects any mapped object that is:
    (a) not within a configured distance from the current location;
    (b) not within a configured search cone from the current location in the direction;
    (c) not within a configured search depth for the current location and direction.

6. The explorer device of claim 1, wherein the location service is further operable to provide information indicating a location of the explorer device, and wherein the processor is further configured to, when the explorer device is not within an indoor location:
    (a) determine the current location of the explorer device based upon a set of location data from the location service;
    (b) determine the direction that the explorer device is directed in based upon the set of direction data from the location service;
    (c) identify the set of mapped objects within the set of remote indicator data based on the direction and the current location; and
    (d) announce each of the set of mapped objects via the audio device.

7. The explorer device of claim 6, further comprising a user interface device, wherein the processor is further configured to provide a virtual exploration in response to receiving an input via the user interface device and wherein the processor is configured to, when providing the virtual exploration:
    (a) receive a virtual origin via the user input;
    (b) where the virtual origin is an indoor location, set the initial value of the current location, the level, and the direction based on the virtual origin; and
    (c) where the virtual origin is an outdoor location, set the initial value of the current location and the direction based on the virtual origin.

8. The explorer device of claim 6, wherein the processor is further configured to, when the explorer device is not within an indoor location:
    (a) determine a location of the nearest location indicator based upon the current location and the set of remote indicator data; and
    (b) if the location of the nearest location indicators is not within a configured distance of the current location, configure the indicator monitor to operate in a reduced power state and thereby reduce power consumption of the explorer device.

9. The explorer device of claim 6, wherein the set of remote indicator data comprises a set of indoor location data and a set of outdoor location data, and wherein the processor is further configured to:
    (a) when identifying the set of mapped objects while in an indoor location, exclude the set of outdoor location data; and
    (b) when identifying the set of mapped objects while not in an indoor location, exclude the set of indoor location data.

10. The explorer device of claim 1, wherein the processor is further configured to:
    (a) receive a set of local indicator data from a location indicator that is associated with a new level other than the level;
    (b) announce the new level via the audio device;
    (c) identify a new set of mapped objects within the set of remote indicator data based on the direction, the current location, and the new level; and
    (d) announce each of the new set of mapped objects via the audio device.

11. The explorer device of claim 1, wherein the processor is further configured to, when identifying the set of mapped objects:
    (a) determine the orientation of the explorer device using the location service;
    (b) select a current interface mode from a set of interface modes based upon the orientation; and
    (c) identify the set of mapped objects based on the direction, the current location, the level, and the current interface mode;
    wherein the set of interfaces modes comprises at least three interface modes.

12. The explorer device of claim 11, wherein the set of interface modes comprises a flat mode, a portrait mode, and a landscape mode.

13. The explorer device of claim 1, wherein the processor is further configured to transmit a locater signal to a location indicator of the set of location indicators, wherein the locator signal is configured to cause the location indicator to emit an audible tone.

14. A method comprising:
    (a) when an explorer device is in an indoor location, determining a direction that the explorer device is directed in based upon a set of direction data from a location service of the explorer device;
    (b) receiving a set of local data from each of a set of location indicators that are within range of an indicator monitor of the explorer device;
    (c) determining a current location of the explorer device and a level of an indoor structure that the explorer device is on based upon:
        (i) the set of local indicator data for each of the set of location indicators; and
        (ii) a set of remote indicator data;
    (d) identifying a set of mapped objects within the set of remote indicator data based on the direction, the current location, and the level, wherein each of the set of mapped objects corresponds to and describes a physical object or a physical location; and
    (e) announcing each of the set of mapped objects via an audio device of the explorer device.

15. The method of claim 14, wherein the set of location indicators comprises at least three location indicators, further comprising, when determining the current location of the explorer device and the level of the indoor structure:
    (a) determining a unique identifier for each of the set of location indicators based upon the set of local indicator data for each of the set of location indicators;
    (b) using the set of remote indicator data and the unique identifier for each of the set of location indicators:
        (i) determining a latitude and a longitude associated with each of the set of location indicators; and (ii) determining the level based upon an association with at least one of the set of location indicators;

(c) determining a distance between the explorer device and each of the set of location indicators based on the set of local indicator data for each of the set of location indicators; and (d) determining the location of the explorer device based upon a trilateration of the distance between the explorer device and each of the set of location indicators and the latitude and longitude for at least one of the set of location indicators.

16. The method of claim 14, further comprising:

(a) determining that the explorer device is connected to a braille display;

(b) determining a number of braille cells associated with the braille display; and (c) configuring an output device of the explorer device to limit text output based on the number of braille cells associated with the braille display.

17. The method of claim 14, wherein the location service is further operable to provide information indicating a location of the explorer device, further comprising, when the explorer device is not within an indoor location:

(a) determining the current location of the explorer device based upon a set of location data from the location service;

(b) determining the direction that explorer device is directed in based upon the set of direction data from the location service;

(c) identifying the set of mapped objects within the set of remote indicator data based on the direction and the current location; and (d) announcing each of the set of mapped objects via the audio device.

18. The method of claim 17, further comprising providing a virtual exploration in response to receiving an input via a user input of the explorer device, further comprising, when providing the virtual exploration:

(a) receiving a virtual origin via the user input;

(b) where the virtual origin is an indoor location, setting the initial value of the current location, the level, and the direction based on the virtual origin; and (c) where the virtual origin is an outdoor location, setting the initial value of the current location and the direction based on the virtual origin.

19. The method of claim 17, further comprising, when the explorer device is not within an indoor location:

(a) determining a location of the nearest location indicator based upon the current location and the set of remote indicator data; and (b) if the location of the nearest location indicators is not within a configured distance of the current location, configuring the indicator monitor to operate in a reduced power state.

\* \* \* \* \*